United States Patent [19]
Arfors

[11] Patent Number: 4,797,277
[45] Date of Patent: Jan. 10, 1989

[54] METHOD FOR REPERFUSION THERAPY

[75] Inventor: Karl E. Arfors, del Mar, Calif.

[73] Assignee: Pharmacia AB, Uppsala, Sweden

[21] Appl. No.: 99,403

[22] Filed: Sep. 22, 1987

[51] Int. Cl.$^4$ .............................................. A61K 39/00
[52] U.S. Cl. ...................................... 424/85.8; 435/1; 514/2; 514/21
[58] Field of Search .................. 424/85; 435/1; 514/2, 514/21

[56] References Cited
PUBLICATIONS

Schwartz et al.—Chem. Abst., vol. 103, (1985), p. 51847j.
Wallis et al.—Chem. Abst., vol. 104, (1986, p. 223374s).

*Primary Examiner*—Sam Rosen
*Attorney, Agent, or Firm*—Fred Philpitt

[57] ABSTRACT

Method for reperfusion therapy of a mammalian organ comprising the step of administering systemically to said organ a therapeutically active amount of an antibody preparation having specificity for a LAC-epitope that is responsible for leukocyte-endothelial cell adherence.

7 Claims, No Drawings

METHOD FOR REPERFUSION THERAPY

TECHNICAL FIELD

This invention relates to method and means for treating mammalian organs that potentially suffer from ischemia so that ischemia/reperfusion (I/R)-induced tissue damage can be prevented. The rationale behind the invention is to block biospecifically the adherence of leukocytes, such as polymorphonuclear leukocytes (PMNs), to endothelial cells in the microcirculation.

Ischemia is a condition that occurs in organs suffering from an obstructed blood flow. Ischemic conditions that are not rapidly abolished may lead to cell death and may be fatal for the organ or individual involved. Since quite a long time it has been recognized that the reperfusion of an organ suffering from ischemia may lead to I/R-induced tissue damage in a variety of clinical conditions like coronary infarction, organ transplantation, shock etc.

SCIENTIFIC BACKGROUND

There is now a substantial body of evidence indicating that reactive oxygen metabolites (=ROM) and PMNs mediate ischemia/reperfusion (I/R)-induced tissue damage (Korthuis and Granger, 1986; Hearse et al., 1986).

Several studies have indicated that certain enzymes may be involved in the production in vivo of oxygen radicals like $O_2^-$ and $HO^.$ and thereby being import mediators of I/R-induced tissue damage. Most of the interests has been focused on xanthine oxidase, an enzyme existing in intestinal epithelia and vascular endothelium. Due to the central role that ROM has in I/R-induced injury, it has been proposed to administer substances acting as oxygen radical scavengers and agents inhibiting radical producing enzymes in order to prevent this type of injury. Positive effects have been achieved but they have not been satisfactory.

The PMNs have been suggested to cause injury following ischemia and reperfusion in the myocardium (Romson et al., 1983; Engler et al., 1983; Schmid-Schoenbein & Engler, 1987) hemorrhagic shock induced gastric mucosal injury (Smith et al., 1987), skeletal muscle (Bagge et al., 1980), and the brain (Grögaard et al., 1987). The mechanism by which the PMNs cause I/R injury has been suggested to be mechanical plugging of capillaries giving as a consequence a reduced blood flow (Schmid-Schoenbein & Engler, 1987; Smith et al., 1987) and/or release of tissue damaging substances like reactive oxygen metabolites (Korthuis & Granger, 1986), cationic proteins (Henson & Johnston, 1987), and proteases (Harlan, 1985) respectively.

The cause of PMN infiltration to the ischemic area is more open to debate. Dead or damaged tissue is known to have chemotactic activity itself (O'Flaherty & Ward, 1979) or indirectly by activating the complement system. Further, during hypoxia xanthine dehydrogenase is converted to xanthine oxidase, which further reacts with hypoxanthine to form xanthine and urea, thereby producing superoxide (Granger et al., 1981). Superoxide can bring about oxidative changes in arachidonic acid resulting in the appearance of a chemotactic lipid (Perez et al., 1980; Petrone et al., 1980). The involvement of xanthine oxidase in I/R injury is supported by the beneficial effect xanthine oxidase inhibitors (i.e. allopurinol) have on I/R tissue damage (Grisham et al., 1986), thus supporting an important role for a superoxide induced chemotactic lipid.

After the finding that adherence of PMNs is critical for the development of I/R-induced injury much interest has been focused on leukocyte-endothelial vascular interactions. This phenomenon is very complex and has been reviewed by several authors (e.g. Harlan, 1985).

The membrane leukocyte adhesion complex (LAC) is critical for the in vitro (Harlan et al., 1985) and in vivo (Arfors et al., 1987) adherence of stimulated PMNs to endothelial cells. Patients deficient in LAC, or parts thereof, have recurrent infections without pus formation, and their PMNs do not adhere to endothelium in vitro.

LACs consists of three subunits: LFA-1 being expressed on lymphocytes and monocytes, Mac-1 on granulocytes and monocytes, and p150.95 on macrophages and monocytes. Each subunit consists of one common beta-chain (CD18) and an alpha-chain that is unique for each of the three subunits (CD11a, CD11b, and CD11c, respectively). The LAC complex has been extensivel studied (Sanches-Madrid et al., 1983) and designated LFA-1/Mac-1/p150.95 (Bernstein and Self, 1985). Several monoclonal antibodies (MoAb) have been raised against its different epitopes. Some of them such as MoAb 60.3, IB4, CL54 etc have been shown to block leukocyte adherence to endothelial cells both in vivo and in vitro. In particular MoAbs that inhibit leukocyte adherence bind to the beta-chain, but the alpha-chain may also be involved in the adherence by providing part of the binding epitope on LAC. The epitope responsible for adherence may be exposed on the leukocytes due to a conformation change in the beta-chain and possible also in the alpha-chain. The most extensively studied MoAb having an inhibitory effect on leukocyte adherence to endothelial cells is MoAb 60.3, and addition of MoAb 60.3 to normal PMNs induces in vitro defects in PMN spreading, adherence, and chemotaxis similar to those observed in LAC-deficient patients. Furthermore, MoAb 60.3 has been shown to inhibit PMN accumulation and plasma leakage in rabbit skin inflammatory lesions. The above results with MoAb 60.3 have been published (Arfors et al., 1987; Beatty et al., 1984; Harlan et al., 1985; Diener et al., 1985; Pohlman et al., 1986; and Wallis et al., 1986). IB4 has been described (Wright et al., 1983; van Voorhis et al., 1983) as well as CL54.

THE INVENTION

The objective of the present invention is an improved method for reperfusion therapy. Its ultimate goal is to selectively prevent leukocytes from biospecifically adhering to vascular endothelial cells in injured tissue, thereby minimizing tissue damages that have been causally related to the formation of reactive oxygen metabolites and/or proteases.

This objective can be achieved by administering to a mammalian organ, suspected of being subjected to ischemia and in connection with reperfusion therapy a pharmaceutical compositon containing a therapeutically active amount of an antibody preparation specific for a LAC-epitope that is responsible for leukocyte-endothelial cell adherence. The specificity above means that the antibody preparation is substantially free from antibodies having other specifities. The expression "in connection with reperfusion therapy" means that the composition can be administered before, after or simultaneous with a reperfusion.

The term antibody shall be understood in a broad sense. It encompasses also other components having biospecific affinity for the epitopes in question. Thus modified and/or fragmented antibodies (Fab, F(ab')$_2$ and Fab$_2$) directed against the epitopes in question and synthetic compounds mimicrying this specificity are contemplated. In the patent literature compounds exhibiting one and the same biospecific affinity usually are taken together under the common name receptor or ligand and treated as being equivalents.

A subordinate objective of the invention is to use an antibody preparation having the specificity above, for the preparation of a composition for use in reperfusion therapy.

The antibody preparation may be an immunosorbent purified polyclonal antibody, but in the preferred case it is a monoclonal antibody directed against one of the epitopes in question, for instance that of MoAb 60.3, IB4, CL54 etc. In the case of monoclonal antibodies, a more efficient treatment can be achieved, because they inherently only block LAC-related leukocyte functions leaving other cell functions intact. By the use of an antibody-active fragment devoided of its Fc-portion or conjugated to certain water-soluble polymers like polyethylene glykol it might be possible to reduce potential adverse effects like immunogenicity.

The invention is primarily concerned with the treatment of humans, although organs dissected from humans and reperfused may be subjected to the invention. The administration is preferably systemic, i.e. the composition is given in such a way that its antibody active components can reach the circulation without being substantially inactivated. This can be achieved by intravenous infusion. Alternatively by subcutaneous, intraperitoneal or intramuscular injection. In certain cases it may be necessary to give repeated administrations depending on inter alia the metabolism of the receptor given and severeness of the ischemic condition treated. Intramuscular injections may give rise to depot effects minimizing the need of repeated administrations. The composition should mostly be given in the form of a sterile aqueous solution buffered to physiologically acceptable pH, e.g. phosphate buffered saline. The composition can be sold as the previously mentioned solutions or in a freeze- or spray-dried form to be reconstituted immediately prior to its use. The amount of antibody in the composition depends on the type and quality and the body weight of the individual to be treated. For intact antibodies the rule of thumb is 0,01–5 mg active components per kg body weight. According to our knowledge of today the preferred range is 0,1–1 mg or in certain cases 0,1–2 mg. A F(ab)$_2$-fragment will require a lower dose than the intact antibody, providing they are of the same Ig-class, affinity, and animal origin. A receptor of high affinity will mostly require a lower dose than one having a lower affinity.

Since most antibodies available are heterologous to humans, overdosing within the weight range given above should be avoided. It can result in anaphalactic reactions.

The composition of the invention may be part of a prepacked kit containing therpeutics useful for the treatment of different aspects of ischemia/reperfusion, so-called multi-factorial treatment. As has been indicated above reperfusion damage can appear when an obstructed blood-flow is cleared giving as a consequence the release of ROM, cationic proteins and proteases. Thus therapeutically active free radical scavenger or other substances decreasing ROM concentration in vivo or protease inhibitors can be present in the kit contemplated. In one potentially very important mode of the invention, the composition is prepacked together with a thrombolyticum, such as an enzyme facilitating blood clot degradation like urokinase, streptokinase or TPA (tissue plasminogen activator).

The claimed patent rights is defined in the appended claims. The invention will now be illustrated by ways of the scientific work enabling the conclusion that the use of certain anti-LAC antibodies will provide in a favourable method for reperfusion therapy.

METHODS

Surgical Procedure

The experimental preparation used in this study is similar, except for minor modifications to that described in detail in previous studies (Granger 81, Parks 83). Briefly, 20 cats previously fasted for 18–24 hours were initially anesthetized with 50 mg/kg Ketamine-HCl. The right femoral artery and vein were cannulated and anesthesia was maintained by administration of sodium pentobarbital into the femoral vein. Systemic arterial pressure was measured with a Statham P23A transducer (Statham, Oxnard, Calif., USA) that was connected to a carotid artery cannula. A tracheotomy was performed to facilitate breathing and as a means of artificial ventilation if the cats failed to breathe spontaneously during the experiment.

A midline abdominal incision was made and a 15–20 cm segment of ileum was isolated; blood and lymph vessels were maintained intact. The remainder of the small and large intestine was extirpated. Immediately after isolation of the ileal segment and before cannulation of the lymphatic and blood vessels, heparin (1,000 U/kg) was administered intravenously. Body and gut temperatures were maintained at 37° C. with thermistor-controlled infrared lamps. To minimize evaporation and tissue-dehydration, the intestinal segment was moistened with saline-soaked gauze and placed in a plastic bag.

A large prenodal lymphatic vessel draining the intestinal segment was cannulated, and lymph flow was determined by observing the movement of lymph in a calibrated micropipette (50–1,000 µl). Lymph ($C_L$) and plasma ($C_p$) total protein concentrations were measured with a calibrated refractometer (American Optical Corp., Buffalo, N.Y., USA). A large cannula was inserted into the superior mesenteric vein, and venous outflow drained into a reservoir mounted on a vertically positioned pulley system. Blood from the reservoir was returned to the animal via the femoral vein cannula. Venous outflow pressure of the intestinal segment was set by adjusting the height of the reservoir and was monitored from a T-connector in the venous circuit. Control venous pressure was set at 0 mmHg. Intestinal blood flow was periodically measured by timed collection of venous effluent in a graduated cylinder.

An arterial circuit was established between the superior mesenteric and femoral arteries. Superior mesenteric arterial pressure was measured via a T-tube interposed within the arterial circuit using a Statham P23A transducer. All pressure cannulas and associated transducers were positioned at heart level. Heparinized whole blood from a donor animal was used to prime all the extracorporeal blood circuits. Systemic and superior mesenteric arterial pressures and venous pressure were continually recorded with a Grass physiologic recorder (Grass Instrument Co., Quincy, Mass., USA). At the end of each experiment the intestinal segment was weighed. Lymph flow and blood flow were normalized to milliliters per minute per 100 g tissue.

Experimental Protocols

In all experiments, control values for intestinal blood flow, lymph flow, and lymph and plasma protein concentrations were obtained at a normal local arterial pressure (90–120 mmHg) and at a venous pressure of 0 mmHg. The animals then received either 1,0 ml neutrophil antiserum (n=6), 2 mg/kg of the murine monoclonal antibody MoAb60.3 (n=6), nonimmune serum (n=4) or saline (n=4) (Genetic System, Seattle, Wash., USA), injected directly into the superior mesenteric arterial loop. Since the saline and non-immune serum treated groups were not significantly different, the data were pooled.

Aliquots of whole blood (50 $\mu$l) were obtained during the control period and every hour thereafter. The blood samples were diluted with 3% (140 $\mu$l) acetic acid to lyse erythrocytes. Nuclei of the leukocytes were stained with 1.0% crystal violet (10 $\mu$l) and polymorphonuclear (neutrophils) and mononuclear (lymphocytes, monocytes) leukocytes were counted using a hemocytometer. Neutrophil counts were expressed as cells per ml of whole blood.

One hour after the administration of neutrophil antiserum, MoAb 60.3 nonimmune serum or saline, local arterial pressure was lowered using an adjustable clamp to partially occlude the local arterial circuit, such that intestinal blood flow was reduced to 15–20% of the control value. Blood flow was maintained at this level for one hour. After 60 min of ischemia, the intestine was reperfused by releasing the partial arterial occlusion. Once all measured parameters reached a new steady-state, venous pressure was elevated in 10 mmHg increments up to 40 mmHg. Intestinal venous pressure was maintained constant at each pressure level until all parameters (lymph flow, $D_L$, $C_P$) were in a steady-state. This procedure was used in all ischemia/reperfusion (I/R) experiments. The same protocol was used for control estimates of microvascular permeability, with the exception that the intestine was not subjected to a period of ischemia.

Microvascular Permeability Estimates

The osmotic reflection coefficient ($\sigma_d$) of intestinal capillaries was estimated using the steady-state relationship between the lymph-to-plasma protein concentration ratio ($C_L/C_P$) and lymph flow (Granger et al., 1981; Parks and Granger, 1983). As lymph flow is increased, $C_L/C_P$ rapidly decreases (filtration rate-dependent) and then becomes relatively constant at a minimal value (filtration rate-independent) when lymph flow is high. At low venous pressures, the exchange of macromolecules across the intestinal capillary wall occurs by both diffusion and convection. Elevation of venous pressure increases the convective movement of macromolecules across the capillary wall while at the same time the diffusive contribution to total exchange is reduced to a negligible level. Theoretical and experimental evidence suggests that $\sigma_d = 1 - C_L/C_P$ when $C_L/C_P$ is filtration rate-independent, i.e., when diffusive exchange is negligible (Granger and Taylor, 1980; Taylor and Granger, 1984). In the present study, microvascular permeability was expressed as 1-$\sigma_d$.

Preparation of Antiserum to Feline Polymorphonuclear Leukocytes (Neutrophils)

Pooled antiserum to feline neutrophils was raised in four New Zealand white rabbits. Briefly, neutrophils and mononuclear leukocytes were purified by the method of Grisham et al. (Grisham et al., 1985) in which erythrocytes were sedimented with dextran while mononuclear and polymorphonuclear leukocytes were separated from each other on a Histopaque 1 077 gradient. Contaminating erythrocytes were removed by hypotonic lysis. Neutrophils prepared by this method were greater than 90% pure with the other 10% composed of monocytes and an occassional eosinophil. Eight milliliters of washed neutrophils ($2 \times 10^7$ cells/ml) was mixed with 8 mls of Freunds complete adjuvant for subcutaneous immunization. Each rabbit received a booster injection of neutrophils ($4 \times 10^7$) in Freunds incomplete adjuvant twenty-one days after the initial injection. Ten days later serum was collected, heat inactivated (56° C. for 30 min) and exhaustively absorbed against feline pooled erythrocytes and the mononuclear leukocyte fraction. Immunoglobulins were precipitated by $(NH_4)_2SO_4$ fractionation (40%), and dialyzed against 4 liters of phosphate buffered saline for 48 hours at 4° C. The antibody agglutination titer against purified feline neutrophils was assessed using serial dilutions of the IgG fraction. The highest dilution that showed agglutination of 5 or more cells was 1:1024. This IgG antineutrophil fraction was stored at −20° C. for subsequent use. Nonimmune serum was generated from plasma obtained from nonimmunized rabbits which was treated in the above manner.

Neutrophil Adherence

A monoclonal antibody (MoAb 60.3) to LAC (CD18) was tested for its effect on adherence of feline neutrophils using the method of Fehr and Dahinden. Briefly, one ml aliquots of neutrophils ($2 \times 10^6$ cells/ml, in heat-inactivated plasma) were placed into wells of tissue culture plates containing varying concentrations of MoAb 60.3. Plates were incubated for 40 min at 37° C. Each well was then gently rinsed three times with one column of ice cold phosphate buffered saline. Neutrophil adherence was assessed by measuring the myeloperoxidase activity (MPO) of the neutrophil suspensions added to wells as well as the MPO of neutrophils adhering to the plastic wells following washing. Neutrophil adherence was expressed as per cent adherent cells.

RESULTS

Our results (Table 1) indicate that prevention of neutrophil adherence with moAb 60.3 affords significant protection against I/R-induced microvascular injury. The observation that neutrophil depletion and prevention of neutrophil adherence are equally effective in attenuating the microvascular injury suggests that neutrophil adherence is the rate-limiting step in neutrophil-mediated microvascular injury.

The control means white blood cell count for all experiments was $1.59 \pm 0.13 \times 10^7$ cells/ml of blood. In ANS-treated cats, neutrophil depletion was maximal (less 5% of control) 1 hr after treatment and remained below 10% of control for the next 3 hrs. Blood neutrophil count increased to 150% in the MoAb and to 120% in the non-immune serum-treated groups 1 hour after treatment.

MoAb 60.3 caused a dose-related reduction in cat neutrophil adherence in vitro. The maximal response (80% reduction) to MoAb 60.3 was observed at concentrations $\geq 5$ μg/ml. It is estimated that the dose of MoAb used in the in vivo studies (2 mg/kg) roughly corresponds with the 50 μg/ml in vitro.

Table 1 summarizes the microvascular permeability data obtained in the various experimental groups. The results indicate that neutrophil depletion with ANS or prevention of neutrophil adherence with MoAb 60.3 significantly attenuate the increased microvascular permeability induced by I/R.

TABLE 1

Effects of antineutrophil serum (ANS) and MoAb 60.3 treatment on ischemia-reperfusion (I/R)-induced changes in microvascular permeability

| Experimental Group | Microvascular Permeability $(1-d)^*$ | Significance relative to: Control | Significance relative to: I/R |
|---|---|---|---|
| Control | 0.08 ± 0.007 | — | $p < 0.001$ |
| I/R-saline or non-immune serum | 0.32 ± 0.02 | $p < 0.001$ | — |
| I/R-ANS | 0.13 ± 0.01 | $p < 0.05$ | $p < 0.001$ |
| I/R-MoAb 60.3 | 0.12 ± 0.003 | $p < 0.05$ | $p < 0.001$ |

*means ± SEM

References

Arfors, K-E. et al., Blood 69:338–40, 1987.
Bagge, U. et al., Acta Physiol. Scand., 180:159–63, 1980.
Bernstein, I. D. and S. Self; In: Leucocyte Typing II; New York, Springer Verlag 1985 p. 1 (Ed: Reinherz, E. L. et al.).
Beatty, P. G. et al., Lancet 1:535–7, 1984.
Diener, A. M. et al., J. Immunol. 135:537–43, 1985.
Engler, R. L. et al., Am. J. Pathol. 111:98–111, 1983.
Fehr, J., and C. Dahinden, J. Clin. Invest. 64:8–16, 1979.
Granger, D. N., and A. E. Raylor, Am. J. Physiol. 238 (Heart Circ. Physiol. 7):H457–H464, 1980.
Granger, D. N. et al., Gastroenterology 81:22–29, 1981.
Grisham, M. B. et al., J. Immunol. Methods 82:315–320, 1985.
Grisham, M. B. et al., Am. J. Physiol. 251:G567–574, 1986.
Grögaard B. et al., in Novelli, Ursini (eds.), Oxygen free radicals in shock. Int. Workshop, Florence 1985, pp. 74–78 (Karger, Basel 1986).
Harlan, J. M., Blood 65:513–25, 1985.
Harlan, J. M. et al., Blood 66:167–78, 1985.
Hearse, D. J. et al., Acta Physiol. Scand. 548:65–78, 1986.
Henson, P. M. and R. B. Johnston, J. Clin. Invest. 79:669–74, 1987.
Korthuis, R. J., and D. N. Granger., In: Physiology of Oxygen Radicals (A. E. Taylor, S. I. Matalon, P. A. Ward, eds) American Physiological Society, Bethesda, pp. 217–249, 1986.
O'Flaherty, J. T. and P. Ward., Sem. Hematol. 16:163–74, 1979.
Parks, D. A., and D. N. Granger, Am. J. Physiol. 250 (Gastrointest. Liver Physiol. 13):G749–G753, 1986.
Perez, H. D. et al., Inflammation. 4:313–328, 1980.
Petrone, W. F. et al., Proc. Natl. Acad. Sci. USA 77:1159–1163, 1980.
Pohlman, T. H. et al., J. Immunol. 136:4548–53, 1986.
Romson, J. L. et al., Circulation 67:1016–1023, 1983.
Sanches-Madrid, F. et al., J. Exp. Med. 158:1785–1803, 1983.
Schmid-Schonbein, G. W., and R. L. Engler., Am. J. Cardiovasc. Path. 1:15–30, 1987.
Smith, S. M. et al., Gastroenterology in press 1987.
Taylor, A. E., and D. N. Granger., Handbook of Physiology. The Cardiovascular System. Microcirculation, edited by E. M. Renkin and C. C. Michel. Bethesda, Md,: Am. Physiol. Soc., 1984, sect. 2, vol. IV, pt. 1, chapt. 11, p. 467–520.
van Voorhis, W. C. et al., J. Exp. Med. 158:126–45, 1983.
Wallis, W. J. et al., Blood 67:1007–1013, 1986.
Wright, S. D. et al., Proc. Natl. Acad. Sci. USA 80:5699–5703, 1983.

I claim:

1. Method for reperfusion therapy of a mammalian organ comprising the step of administering systemically to said organ a therapeutically active amount of an antibody preparation having specificity for a LAC-epitope that is responsible for leukocyte-endothelial cell adherence.

2. The method of claim 1, wherein the antibody preparation is monoclonal.

3. The method of claim 2, wherein 0.01–5 mg antibody giving the preparation its specificity is administered.

4. The method of claim 1, wherein said antibody preparation is substantially free from antibodies having other specificities.

5. The method of claim 4, wherein said antibody comprises modified antibodies, fragmented antibodies, and synthetic compounds.

6. The method of claim 1, wherein said antibody preparation is selected from the group consisting of polyclonal antibodies and monoclonal antibodies.

7. The method of claim 1, wherein said antibody preparation is selected from the group consisting of MoAb 60.3, IB4, and CL54.

* * * * *